United States Patent
Gordon et al.

(10) Patent No.: US 10,792,462 B2
(45) Date of Patent: Oct. 6, 2020

(54) CONTEXT-SENSITIVE SOUNDSCAPE GENERATION

(71) Applicant: International Business Machines Corporation, Armonk, NY (US)

(72) Inventors: Michael S. Gordon, Yorktown Heights, NY (US); James R. Kozloski, New Fairfiled, CT (US); Ashish Kundu, Elmsford, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 113 days.

(21) Appl. No.: 15/613,947

(22) Filed: Jun. 5, 2017

(65) Prior Publication Data
US 2018/0344968 A1    Dec. 6, 2018

(51) Int. Cl.
| | | |
|---|---|---|
| *A61M 21/02* | (2006.01) | |
| *G06N 20/00* | (2019.01) | |
| *A61M 21/00* | (2006.01) | |
| *H04S 7/00* | (2006.01) | |
| *H04R 5/04* | (2006.01) | |

(52) U.S. Cl.
CPC ............ *A61M 21/02* (2013.01); *G06N 20/00* (2019.01); *H04S 7/30* (2013.01); *A61M 2021/0027* (2013.01); *A61M 2205/42* (2013.01); *A61M 2205/502* (2013.01); *H04R 5/04* (2013.01)

(58) Field of Classification Search
CPC .................. A61M 21/00; A61M 21/02; A61M 2021/0005; A61M 2021/0027; A61M 2021/0083
See application file for complete search history.

(56) References Cited

U.S. PATENT DOCUMENTS

| | | | |
|---|---|---|---|
| 5,352,181 A | 10/1994 | Davis | |
| 5,356,368 A * | 10/1994 | Monroe | ................ A61M 21/00 |
| | | | 600/28 |
| 7,081,085 B2 | 7/2006 | Viirre et al. | |
| 2009/0208030 A1 | 8/2009 | Anderson et al. | |
| 2013/0338429 A1 | 12/2013 | Gregory et al. | |
| 2015/0222989 A1 | 8/2015 | Labrosse et al. | |
| 2015/0294067 A1* | 10/2015 | Kare | ...................... G16H 10/60 |
| | | | 705/3 |
| 2016/0196758 A1 | 7/2016 | Causevic et al. | |

OTHER PUBLICATIONS

"Rainy Cafe: Ambient White Noise Generator", http://rainycafe.com (retrieved from website on Jun. 1, 2017).
Mehta, R. et al., "Is Noise Always Bad? Exploring the Effects of Ambient Noise on Creative Cognition", Oxford University Press, vol. 39, No. 4, Dec. 2012 pp. 784-799.
https://coffitivity.com/,(retrieved from website on Jun. 1, 2017).

\* cited by examiner

*Primary Examiner* — Carrie R Dorna
(74) *Attorney, Agent, or Firm* — Scully, Scott, Murphy & Presser, P.C.; Kevin M. Jordan, Esq.

(57) ABSTRACT

A context-sensitive soundscape is generated by receiving a first identifier for identifying a target cognitive state for a user, and a second identifier for identifying a user cohort for the user. A present context is determined for the user. A machine-learning procedure is performed to map the target cognitive state to a set of audio output characteristics based upon the identified user cohort and the determined present context. An audio output is generated to create the context-sensitive soundscape that includes the set of audio output characteristics.

20 Claims, 5 Drawing Sheets

CONTEXT-SENSITIVE SOUNDSCAPE GENERATION

FIELD

The present invention generally relates to a context-sensitive generation of sounds, and more particularly relates to a context-sensitive soundscape generation that facilitates a target cognitive state.

BACKGROUND

It is known that naturally recurring sounds of nature, like rainfall or the rolling of the ocean surf, possess the power to calm and soothe. Various techniques that have simulated these natural sounds in indoor environments, both to reproduce their calming and soothing effect and to mask unwanted noise, have often resulted in improved mental concentration and enhanced relaxation. Typically, natural sounds are recorded on media such as long-playing records (LPs), compact discs (CD's), audio cassettes, non-volatile memory such as read-only memory ("ROM"), and "flash" memory and replayed on corresponding sound reproduction equipment, such as a record player, CD player tape deck or cell phone.

SUMMARY

The following summary is merely intended to be exemplary. The summary is not intended to limit the scope of the claims.

One embodiment of the present invention is a computer-implemented method for generating a context-sensitive soundscape. The method comprises receiving, by one or more processors, a user target cognitive state indicia for identifying a target cognitive state, and a user indicia for identifying a user; determining, by one or more processors, a present user context, in response to said receiving a user target cognitive state indicia and a user indicia; performing a machine-learning procedure, by one or more processors, to map the target cognitive state to a set of audio output characteristics; and generating a context-sensitive soundscape with the set of audio output characteristics, based on the user target cognitive state indicia.

Other embodiments include a computer program product and a system.

BRIEF DESCRIPTION OF THE SEVERAL VIEWS OF THE DRAWINGS

The foregoing aspects and other features are explained in the following description, taken in connection with the accompanying drawings, wherein.

DETAILED DESCRIPTION

It is known that certain sounds can be useful in terms of inducing relaxation, promoting falling asleep, increasing creativity, increasing concentration, and/or fostering other cognitive state(s). For example, ambient noise can affect creativity. Compared to a relatively quiet environment (50 decibels), a moderate level of ambient noise (70 dB) may enhance a subject's performance on tasks involving creativity, whereas a high level of noise (85 dB) can have an adverse impact on creativity. Modest background noise is thought to create enough of a distraction to encourage people to think more imaginatively.

Figure 1:
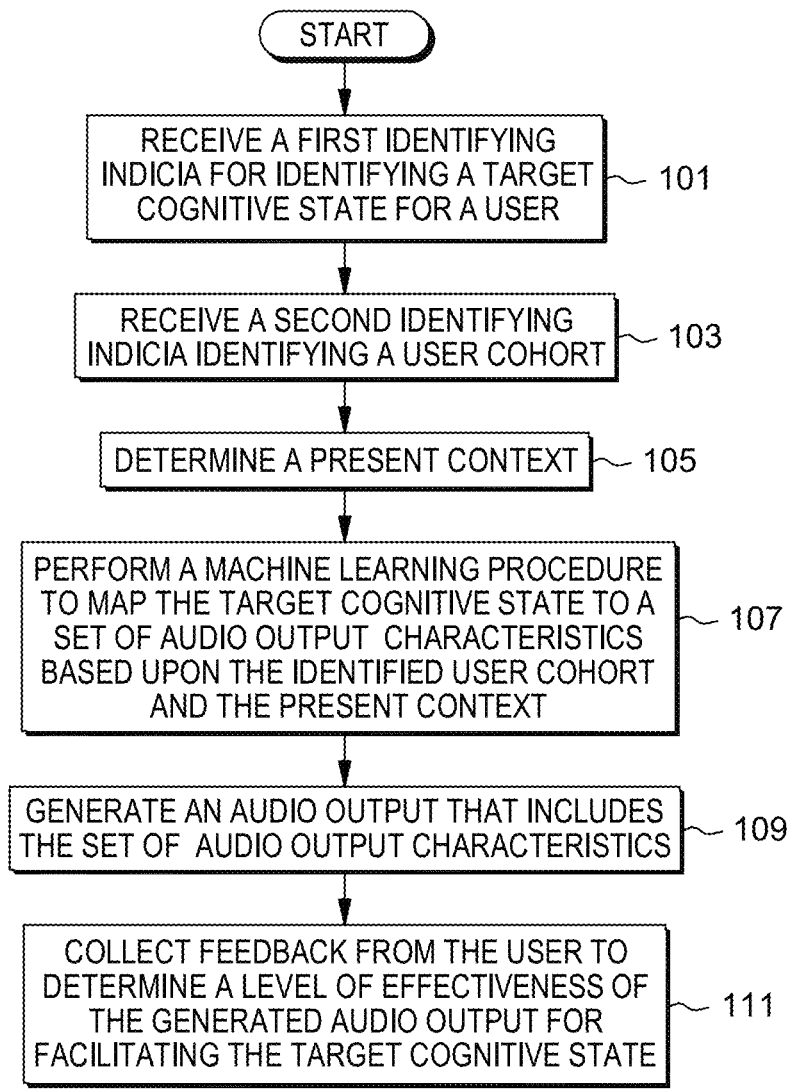
FIG. 1 illustrates an exemplary method for generating a context-sensitive soundscape in accordance with one or more embodiments of the present invention.

FIG. 1 illustrates an exemplary method for generating a context-sensitive soundscape in accordance with one or more embodiments of the present invention. The method commences at block 101 where a target cognitive state indicia is received for a user. By way of example only, a target cognitive state may include any of relaxation, falling asleep, focusing on work, or mental stimulation. Additionally or alternatively, the target cognitive state may be specified in terms of a specific type of sound—such as white or pink noise, or noise having pre-specified spectral properties—that may facilitate achieving the target cognitive state.

The target cognitive state indicia may be received in many different ways. By way of example only, the target cognitive state indicia may be received over a graphical user interface (GUI), a voice command interface, or a gesture interpretation interface. Alternatively or additionally, the first identifying indicia may be determined automatically based on a present context, such as a current time of day, a current location, or a task that a user is inferred to be performing. This task may be inferred or explicitly stated, for example, by receiving information from the user's electronic calendar.

In block 103, a, a user indicia is received. In this example, the user indicia is another (second) indicia of a user cohort. Alternatively or additionally, the user indicia can be an indicia of a specific individual based, for example, on a user profile. A few (non-limiting) examples of user cohorts include: persons having one or more common demographic indicia (such as age, income, ethnicity) persons having one or more common conditions (such as Alzheimer's, autism) persons having one or more common occupations (for example, scientists, engineers, teachers, doctors, students). Alternatively or additionally, the user cohort may include one or more of a culture associated with the user, a spoken language associated with the user, a written language associated with the user, a medical history of the user, or a history for the user of previously using the soundscape generation methods described herein.

Next, at block 105, a present context is determined. The present context may comprise a current time of day, a current location, or a task that a user is inferred to be performing. For example, the current location can be an office space, a bedroom, a waiting room, a store, a library, a hospital, an airplane, a geographic location such as a city and a state, a geographic location as a set of latitude and longitude coordinates, or any of various combinations thereof. The task may be inferred, for example, by receiving information from the user's electronic calendar, and/or by receiving global positioning system (GPS) location information for the user.

The method advances to block 107 where a machine learning procedure is performed to map the target cognitive state to a set of audio output characteristics based upon the identified user cohort and the present context. The machine learning procedure determines which audio output characteristics are useful for achieving the target cognitive state, based on the identified user cohort and the present context. For instance, the machine learning procedure may be configured to include in its assessment: one or more electroencephalogram (EEG) signals received from the user; a voice signal received from the user to determine a stress level associated with the voice signal; identification of a time at which the user falls asleep; a content of a word processing document or a programming code editor; and/or a biometric signal received from the user. Moreover, learning may consider one or more parameters of other users in the identified user cohort, one or more parameters from an identified social network of the user, one or more parameters from a family of the user, or any of various combinations thereof.

In some embodiments, the learning procedure of block 107 (FIG. 1) may include setting a volume level or a sound pressure level (SPL) of the audio output generated at block 109 to enhance, facilitate, or optimize the target cognitive state. In some embodiments—alternatively or in addition to setting the volume level or sound pressure level, the learning procedure of block 107 may include setting a frequency spectrum or a tempo of the audio output (for example, to be generated at block 109) to enhance, facilitate, or optimize the target cognitive state. In some embodiments—alternatively or in addition to setting the volume level or sound pressure level, the learning procedure of block 107 may include a binaural beat (for example, to be generated at block 109) to enhance, facilitate, or optimize the target cognitive state.

A moderate level of noise may enhance creativity to a greater extent than either low or high levels of noise. One explanation is that moderate background noise induces distraction which encourages individuals to think at a higher, abstract level and consequently fosters enhanced creativity and imaginativeness. Accordingly, the moderate ambient noise level in a busy café, restaurant, or coffee shop may perk up an individual's creative cognition. More specifically, when compared to a relatively quiet environment (50 decibels), a moderate level of ambient noise (70 dB) may enhance a subject's performance on creativity tasks, while a high level of noise (85 dB) may adversely impacts the subject's performance. The subject's performance may be used to provide feedback for the learning procedure, including feedback about the effectiveness of the volume level or sound pressure level (SPL) of the audio output generated at block 109 in fostering the target cognitive state.

The extent to which a moderate level of ambient noise fosters creativity can vary according to the user cohort determined at block 103. For example, some user cohorts may prefer to work and study in relatively quiet environments, and these users may be at their most creative with low, not moderate, levels of ambient noise. However, there are also some similarities between different user cohorts. Auditory stimulation for people with Alzheimer's disease and dementia is effective for mood enhancement, relaxation, and cognition, just as it is for everyone else. The calming effects of music are effective on average users as well as users suffering from Alzheimer's disease and dementia. The subject's performance on one or more tests or tasks may be used to provide feedback for the learning procedure, including feedback about the effectiveness of the level of ambient noise in fostering the target cognitive state.

At block 109, an audio output is generated to create the context-sensitive soundscape that includes the set of audio output characteristics. The generated audio output may include, for example, music, environmental sounds, pink noise, white noise, other spectrally-shaped noise, the ambient sounds of people engaged in an activity such as dining in a coffee shop or performing a sport, animal sounds, or any of various combinations thereof. The generated audio output may be fed, for example, to a set of headphones or ear buds, to an earphone, or to a set of one or more loudspeakers.

In some embodiments, one or more parameters of the audio output generated at block 109 may be adjusted or supplemented, such as to incorporate the soothing sounds of fans, rain, waves, crickets, birds, or any of various combinations thereof. In some embodiments, the audio output generated at block 109 may include a plurality of discrete components, where an amplitude of a first component of the discrete components may be adjusted relative to an amplitude of a second component of the discrete components. For example, in situations where the audio output replicates a busy café or restaurant, a first component may be a sound that simulates cutlery making contact with dishes, and a second component may be muffled conversations of various guests or patrons.

At block 111, feedback is collected from the user to determine a level of effectiveness of the generated audio output in facilitating the target cognitive state. For purposes of illustration, the feedback may be collected using a heart rate monitor, an electromyograph, a feedback thermometer, an electrodermograph, an electroencephalograph, a photoplethysmograph, an electrocardiogram, a pneumograph, a capnometer, a rheoencephalograph, hemoencephalography, a blood pressure monitor, a pulse rate monitor, a blood sugar level monitor, an Internet of Things (IoT) biometric sensor, or any of various combinations thereof.

For purposes of illustration, the method of FIG. 1 may be performed in connection with reminiscence music therapy, participatory music and rhythm, sing-alongs, blocking of background sounds with white noise, exercising to music, selecting music in accordance with music associations, agitation management, treatment of late dementia, serving meals, providing health care, giving baths to patients, or administering psychological or medical treatments to patients. Music association refers to the fact that many people associate music with important lifetime events and a wide array of emotions. In the context of agitation management and late dementia, as well as in the context of autism, patients are non-verbal and often become agitated out of frustration and sensory overload from the inability to process environmental stimuli. Engaging these patients in singing, rhythm playing, dancing, physical exercise, and other structured music activities can diffuse this behavior and redirect their attention. When used during meals, soothing music can increase food consumption. When used during bathing, relaxing or favorite music can make it easier to bathe a patient. With older patients, behavioral improvements may be experienced through the use of relaxing, soothing classical, religious or period (1920's or Big Band) music.

Figure 2:
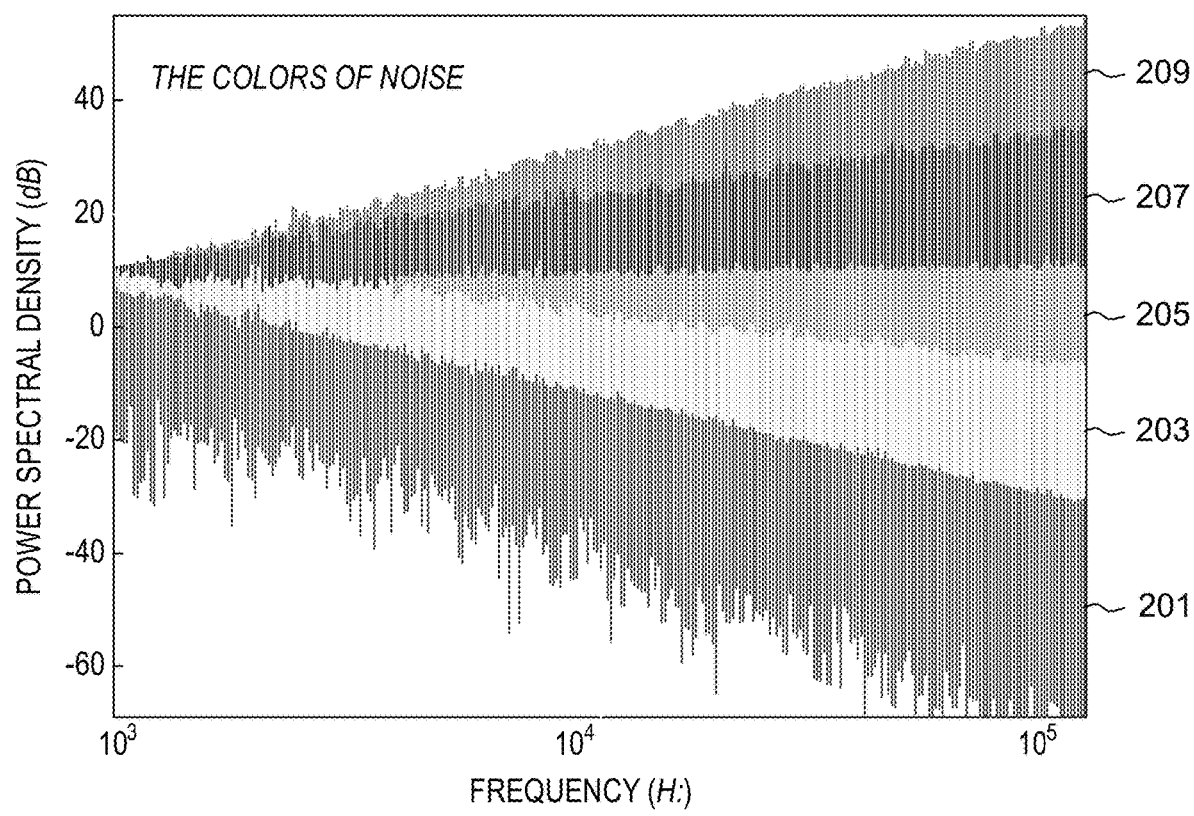
FIG. 2 illustrates an exemplary graph showing power spectral density (PSD) as a function of frequency in accordance with one or more embodiments of the present invention.

FIG. 2 illustrates an exemplary graph showing power spectra density (PSD) as a function of frequency in accordance with one or more embodiments of the present invention. In the example depicted, a graph 200 shows PSD in decibels (dB) as a function of frequency in Hertz (Hz) for several different illustrative audio outputs, which may be generated at block 109 (FIG. 1). Referring specifically now to FIG. 2, the audio output can include characteristics such as: brown noise 201, pink noise 203, white noise 205, azure noise 207, and violet noise 209. The noises 201-209 depicted have been normalized at 1 kHz. The slope of the PSD is −20 dB/decade for brown noise 201, −10 dB/decade for pink noise 203, 0 dB/decade for white noise 205, 10 dB/decade for azure noise 207, and 20 dB/decade for violet noise 209. For purposes of illustration, any of these noises 201-209 may be generated by Cnoise™, an open-source noise generator that is available on Github™, a web-based version control repository and Internet hosting service.

A few exemplary benefits of pink noise 203 may include improved user mental focus, alleviation of headaches, soothing babies and young children, and better quality of sleep. In some embodiments, the pink noise 203 may be synchronized to a user's brain rhythms. This synchronization may cause the user to sleep more deeply and to have increased memory retention.

White noise 205 may perform sound masking/cancellation, and may provide benefits such as improved concentration, and promotion of sleep. Benefits of brown noise 201 may include fostering relaxation and meditation, improving mental focus, enhancing reading comprehension, and improving quality of sleep. By way of further example, white noise 205 or brown noise 201 can be used in the waiting rooms of physicians, dentists, therapists, psychologists and psychiatrists so that the people in the waiting room are not able to hear spoken conversations inside the office.

Figure 3:
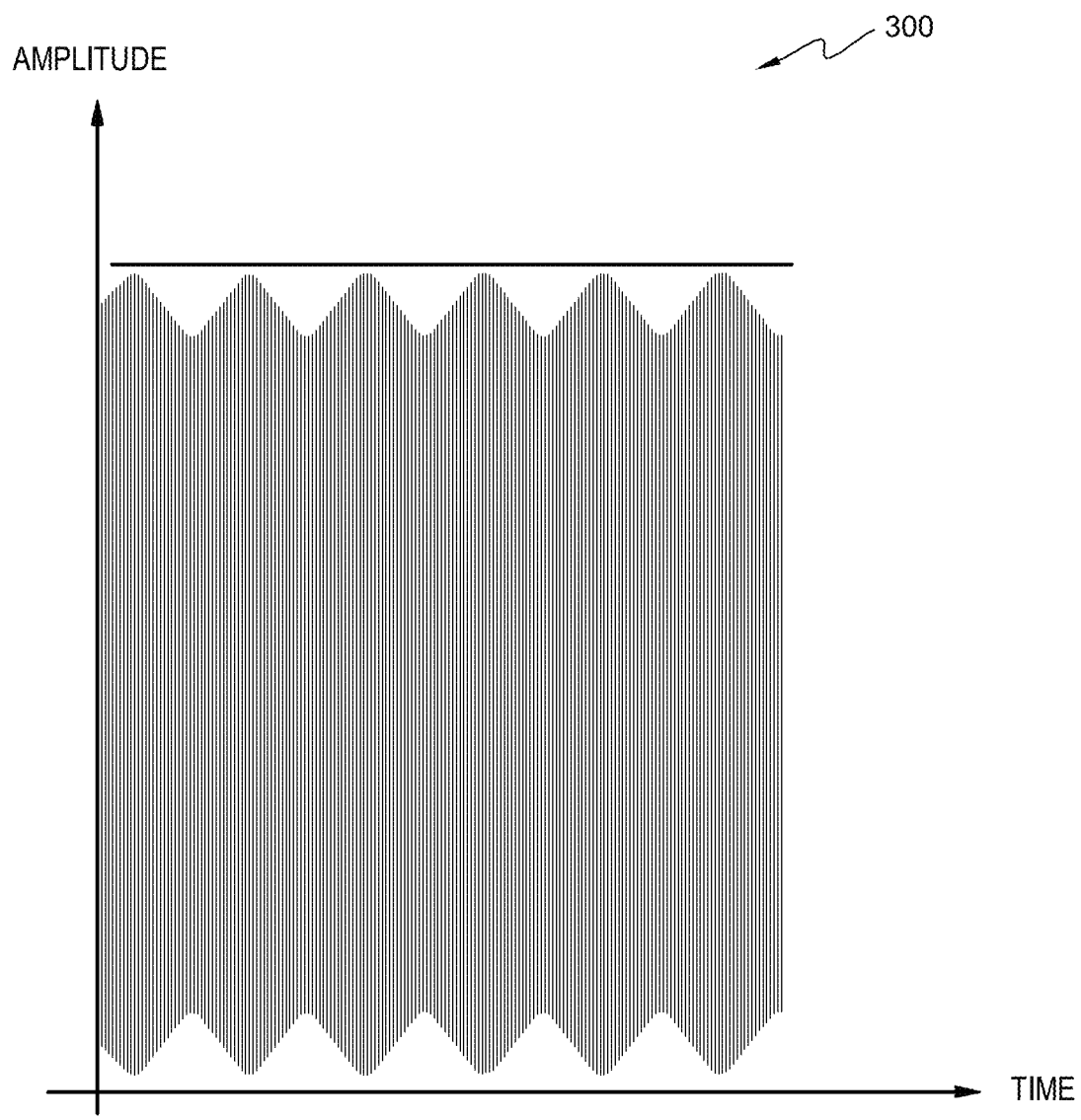
FIG. 3 illustrates an exemplary audio output in the form of a binaural beat in accordance with one or more embodiments of the present invention.

FIG. 3 depicts an exemplary waveform 300 of amplitude versus time for a binaural beat in accordance with the present invention. By way of overview, a binaural beat is an auditory illusion perceived when two different pure-tone sine waves, a first tone and a second tone, both with frequencies lower than 1500 Hz, and with less than a 40-Hz difference between the first and second tones, are presented to a listener separately. For example, the first tone can be fed to a right-side element of a headphone for presentation to a right ear of the user, and the second tone can be fed to a left-side element of the headphone for presentation to a left ear of the user.

As discussed above with regard to the machine learning at block 107 (FIG. 1), an alternative or addition to setting the volume or sound pressure level, block 107 (FIG. 1) may include generating a binaural beat to enhance, facilitate, or optimize the target cognitive state. In some embodiments, the binaural beat may be generated at other blocks e.g., at block 109.

Figure 4:
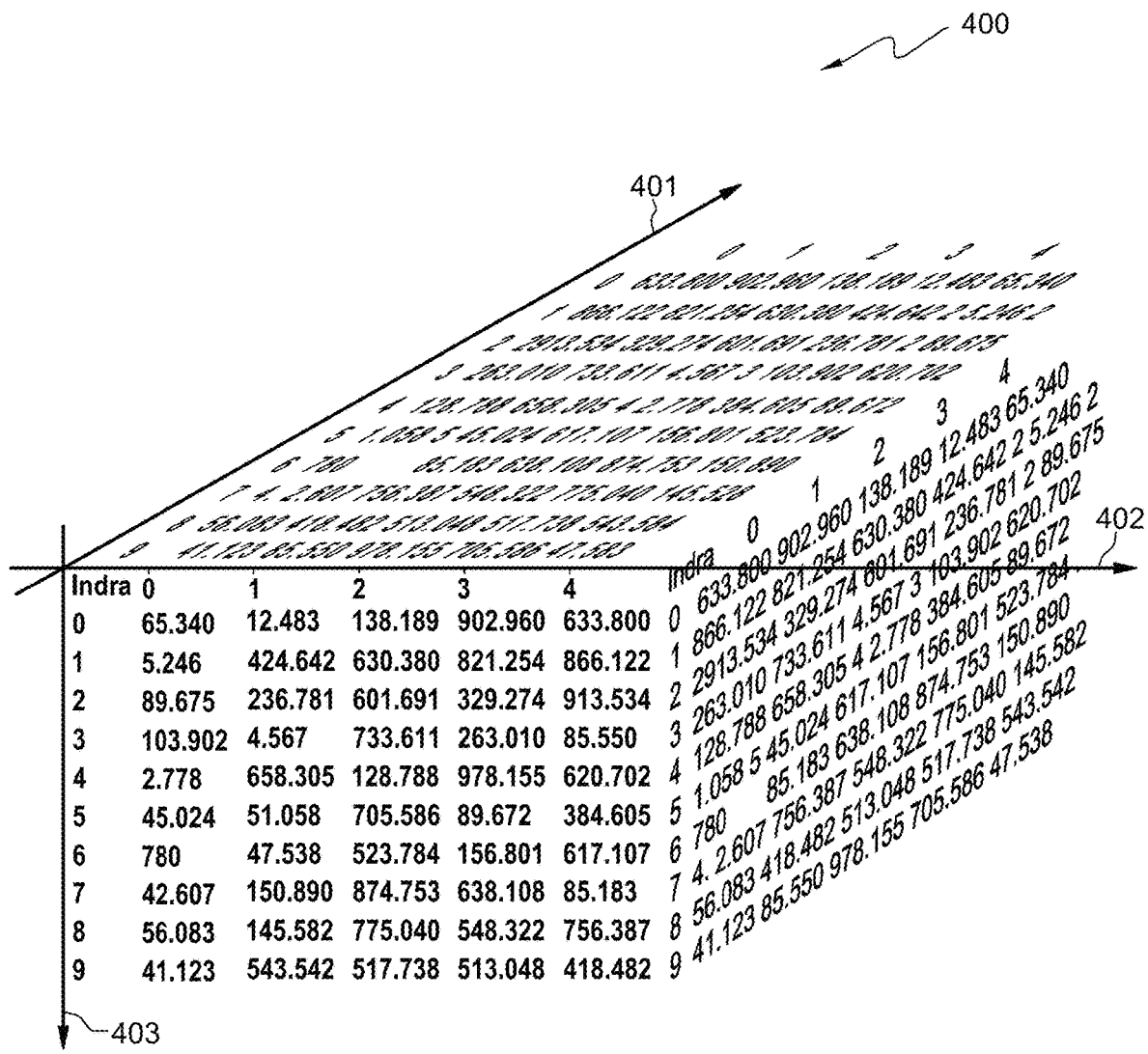
FIG. 4 illustrates an exemplary multi-dimensional array in accordance with one or more embodiments of the present invention.

FIG. 4 illustrates an exemplary multi-dimensional array in accordance with the present invention. As depicted, the multi-dimensional array 400 may be organized along a plurality of axes or dimensions 401, 402, and 403 representing any of a sound identifier (ID), a sound characteristic, a user cohort, a medical or psychological condition, a demographic, a task, a target cognitive state (such as relax/sleep vs. creative), a context (such as on an airplane, in bed, in the office). The multi-dimensional array 400 may be accessed according to learned useful values for an individual or a user cohort. The multi-dimensional array 400 may be configured for associating each of a respective plurality of cognitive states, including the target cognitive state, with at least one corresponding user cohort, at least one corresponding user medical or psychological condition, at least one corresponding user demographic, at least one corresponding task, or at least one context.

Some embodiments of the present invention may have application to pet/animal care. The pet industry is huge, and many owners feel guilty when their pets are left home during the day alone. Of course, sound characteristics for inducing a target cognitive state may be different for animals than for humans. In the case of pets, sound characteristics may include such items as natural sounds or the voice of a pet owner.

According to another set of embodiments, the procedure of FIG. 1 may be employed to learn useful volumes or sound pressure levels (SPLs) for noise masking for two or more different cohorts of users, or for two or more different target cognitive states of users, to provide a real-time adaptive adjustment of sound volume or SPL to provide an optimal or enhanced level of noise masking. For example, ambient noise is generally observed to vary as a function of time. As just one illustration of this observation, an office space is a dynamic site in which ambient noise and the volume of sound distractions vary a great deal depending on the schedule and activities that are underway at any point in time. In some embodiments, the sound masking dynamically adapts to changes in such ambient noise and volume. For example, the volume or SPL of the audio output generated at block 109 (FIG. 1) can be modulated to increase during very active periods, and become softer and more discreet when the area is calmer. In some embodiments, volume and sound pressure levels are collectively referred to as SPLs (for convenience of reference). Optionally, the adaptive adjustment method of FIG. 1 may be configured for identifying variations in ambient noise in real time, from signals supplied by sound level sensors installed in the ambient environment, such as an office ceiling for an indoor environment or a lamp post for an outdoor environment.

According to another set of embodiments, the procedure of FIG. 1 may be employed to learn useful volumes or useful SPLs for noise masking for a specific cohort of user and for a specific target cognitive state of the user. For example, the procedure of FIG. 1 may be applied to athletes, where their performance might improve if certain distracting noises (such as car traffic) were replaced by more soothing background sounds generated at block 109 (FIG. 1). Further, based on geolocation, user profiles, time of day, and day of week, noise levels and types of noise around that geolocation can be modeled and predicted: thus, block 109 may be performed by providing a set of headphones with one or more signals of such undesired noises that are to be cancelled, or altered as needed. These undesired noises may be provided to the set of headphones, for example, by means of a microphone included in or associated with the set of headphones.

The use of signals from undesired noises serves to improve the efficiency and quality of noise cancellation. Further, the user may be traveling from point A to point B using a vehicle or other transportation means. A noise model for that route can be developed and then applied at each location, or between locations, commencing when the user reaches a given location. The user may also specify how to change the sound, a type of sound, the volume, the SPL, or any of various combinations thereof that are generated at block 109 (FIG. 1) dynamically based on time and location on that route. The procedure of FIG. 1 takes the noise models it has acquired from different locations and times, and then takes user requests and collectively decides how to manage the audio outputs and noise cancellations.

According to another set of embodiments, the procedure of FIG. 1 may further include using a set of headphones, a loudspeaker, or another audio transducer to deliver acoustic signals to the ambient sound environment to achieve a particular cognitive outcome. The application of this embodiment is broad. Specifically, the use of algorithmic active noise-canceling circuitry may be employed to shape ambient noise environments to achieve a cognitive outcome. In this way, the source of sound is the ambient environment itself, and the circuitry involved in generating the audio output of block 109 may introduce noise-modulating frequencies into the ambient soundscape in order to create other features. For example, using this embodiment, street noise may be modulated at a delta rhythm (1-4 Hz) in order to induce sleep. Ambient aircraft noise may be modulated at a very low frequency, to induce a sensation similar to that caused by crashing wave.

Alternatively or additionally, noise-cancelling headphones can alleviate fatigue by eliminating repetitive or continued low-frequency noise (such as from a running engine). This phenomenon is likely due to the internal neurophysiology of the brain and the effect of constant low frequency inputs to the primary sensory apparatus and its effects on the cognitive process. One may salvage from the low frequency components to be cancelled a richer set of stimuli that can be left in the generated sound of block 109 asynchronously, or that can be used to achieve an entirely different, stimulating perception, rather than the "droning on" of background low frequency noise.

According to another set of embodiments, the procedure of FIG. 1 may be employed to achieve a modulation of ambient noise in order to effect a cognitive outcome such as improving the accuracy of a speech recognition procedure. By modulating the ambient noise environment using the method of FIG. 1, formants of speech may be elicited in the auditory perceptions of an individual or a computer-executed speech recognition mechanism, thereby facilitating speech recognition. Broadly, this aspect of the invention makes use of noise-vocoded speech algorithms to achieve a useful modulation of the ambient noise environment. Usefulness of this embodiment includes secure channel communication. By making the communication signal a circuit-based function of ambient noise, certain features of the speech are not available even to an eavesdropper.

According to another set of embodiments, the procedure of FIG. 1 may further comprise performing a rhythmic or spectral filtering of background noise in an active circuit in order to induce a perception of music in a user or listener. In this way, musical recordings can be marketed as noise modulated compositions, allowing individuals to enter a state of enjoyment based on modulation of background noise intended to evoke the perception of, for example, classical music, country music, smooth jazz, rockabilly, etc. This approach is based upon a realization that a moderate level of noise enhances creativity compared to both low and high levels of noise. Moderate background noise induces distraction which encourages individuals to think at a higher, abstract level, and consequently exhibit higher creativity.

Figure 5:
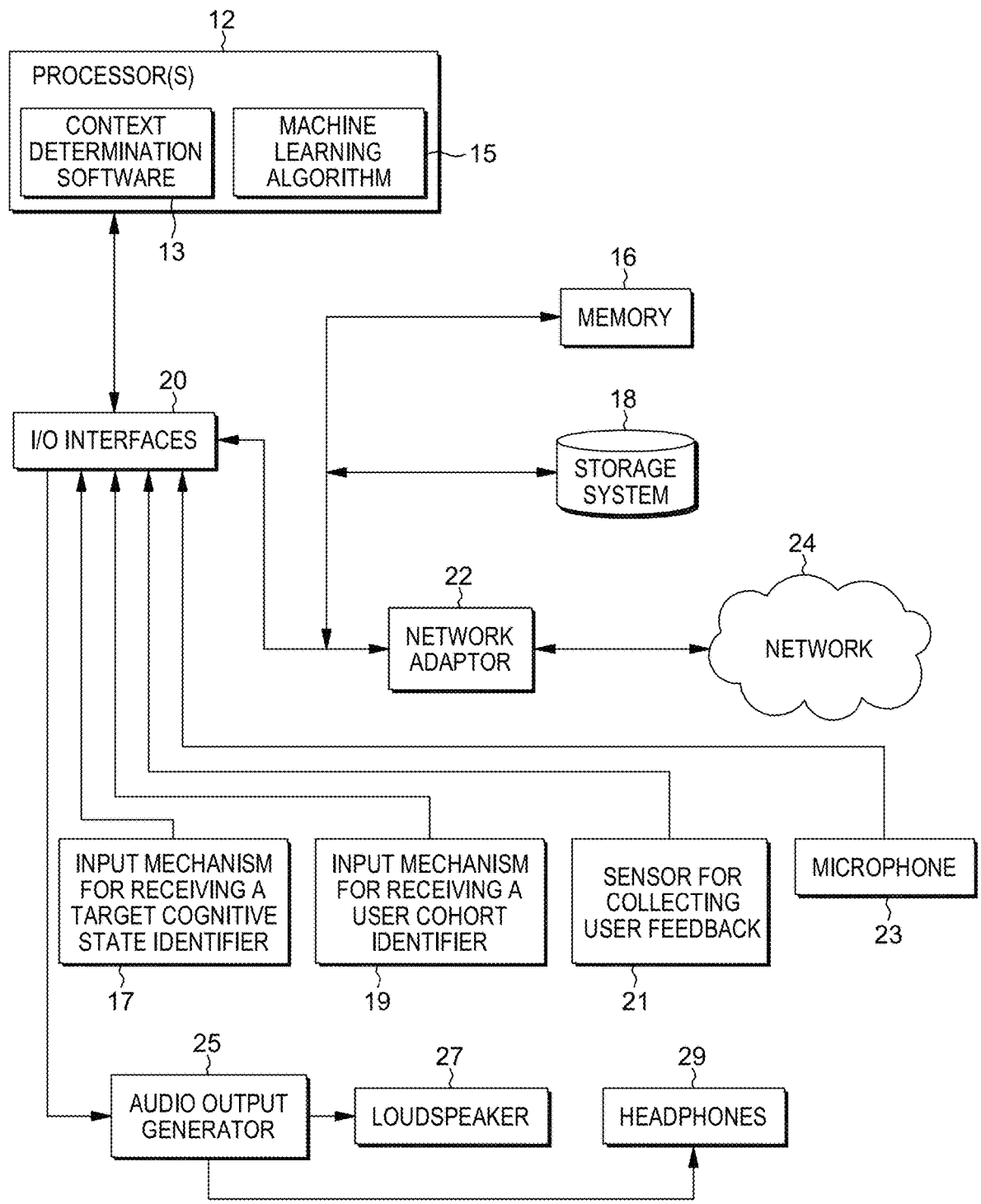
FIG. 5 illustrates an exemplary system for generating a context-sensitive soundscape in accordance with one or more embodiments of the present invention.

FIG. 5 illustrates an exemplary system for generating a context-sensitive soundscape in accordance with one or more embodiments of the present invention. As depicted, the exemplary system includes an input mechanism for receiving a target cognitive state identifier 17, and an input mechanism for receiving a target user cohort identifier 19. The input mechanisms 17, 19 are operatively coupled to a set of I/O interfaces 20 that are further operatively coupled 14 to one or more processors 12. The processor(s) 12 are configured for executing a context determination software 13 and a machine learning algorithm 15 in accordance with the present invention. In some embodiments, the processor(s) 12 execute software/algorithm(s) that are stored in and loaded from storage 18 and memory 16 via a system bus (not depicted).

The input mechanism for receiving the target cognitive state identifier 17 can be used to facilitate block 101 of FIG. 1. The cognitive state identifier can comprise any parameter(s) used to identify a target cognitive state and the parameter may be input to input mechanism 17. A few (non-limiting) examples of an input mechanism 17 include: a keypad, a touch screen, a camera, a speech recognition device, a pointing device, a graphical user interface (GUI), a voice command interface, a gesture interpretation mechanism, or any of various combinations thereof. The parameter could be specified in a form appropriate to the input mechanism, such as a set of numerical characters, alphabetic characters, phrases, sentences, spoken words, gestures, or any of various combinations thereof. For purposes of illustration, the cognitive state may include (without limitation) any of: relaxation, falling asleep, focusing on work, a first cognitive state that is fostered by blocking or cancelling ambient noise, a second cognitive state that is fostered by creating white or pink noise, or a third cognitive state that is fostered by creating noise having pre-specified spectral properties.

The system also includes an input mechanism for receiving the target user cohort identifier 19, which can be used to facilitate block 103 of FIG. 1. In some embodiments, the target user cohort identifier 19 comprises a second identifying indicia for associating a user cohort to a user. The second identifying indicia can comprises any parameter that is used to identify a target user cohort. Similar to the parameter for cognitive state identifier 17, this parameter may be input to the input mechanism 19. A few (non-limiting) examples of an input mechanism 19 include: a keypad, a touch screen, a speech recognition device, a pointing device, a graphical user interface (GUI), a voice command interface, a camera, a gesture interpretation mechanism, or any of various combinations thereof. The parameter could be specified in a form appropriate to the input mechanism 19, such as a set of numerical characters, alphabetic characters, phrases, sentences, spoken words, gestures, or any of various combinations thereof. For illustrative purposes, the user cohort may include any of a student, an autistic person, a computer scientist, an electrical engineer, a teacher, another occupation, a doctor, a patient, a pre-Alzheimer's patient, or a person suffering from a specific medical or psychological affliction. Alternatively or additionally, the user cohort may include a user's culture, a user's language, or a history of previously using one or more of the soundscape generation features or functions of the present invention.

The processor(s) 12 execute the context determination software 13 and the machine learning algorithm 15. The context determination software 13 can facilitate determining a present context for a user, for example, in accordance with the exemplary block 105 of FIG. 1. The present context may comprise a current time of day, a current location, or a task that a user is inferred to be performing. For example, the current location can be an office space, a bedroom, a waiting room, a store, a library, a hospital, an airplane, a geographic location such as a city and a state, a geographic location as a set of latitude and longitude coordinates, or any of various combinations thereof. The task may be inferred, for example, by receiving information from the user's electronic calendar.

The machine learning algorithm 15 (FIG. 5) can be used to facilitate mapping a set of audio output characteristics to the target cognitive state based upon the identified user cohort and the present context, for example, in accordance with the exemplary block 107 of FIG. 1. The machine learning procedure determines which audio output characteristics are useful for approaching the target cognitive state for the identified user cohort and the present context. For instance, the machine learning procedure may be configured for assessing one or more electroencephalogram (EEG) signals received from the user, assessing a voice signal received from the user to determine a stress level associated with the voice signal, identifying a time at which the user falls asleep, assessing a content of a word processing document or a programming code editor, or assessing a biometric signal received from the user. Moreover, learning may be performed by adopting one or more parameters from other users in the identified user cohort, by adopting one or more parameters from a social network of the user, by adopting one or more parameters from a family of the user, or any of various combinations thereof.

A microphone 23 (FIG. 5) operatively coupled to an input of an audio output generator 25 are operatively coupled to the output of I/O interfaces 20. The audio output generator 25 can be used to facilitate generation of the audio output (including the set of audio output characteristics) described with reference to the example of block 109 (FIG. 1). The output of audio output generator 25 may be fed, for example, to a set of headphones 29 (FIG. 5) and/or to a loudspeaker 27, ear buds/earphones or other output device (not depicted). The output generated by the audio output generator 25 may include, for example, music, environmental sounds, pink noise, white noise, other spectrally-shaped noise, the ambient sounds of people dining in a coffee shop, animal sounds, or any of various combinations thereof.

A sensor for collecting user feedback 21 is also operatively coupled to the I/O interfaces 20. The sensor for collecting user feedback 21 collects feedback from the user to determine a level of effectiveness of the audio output generated by the audio output generator 25 for facilitating the target cognitive state. For purposes of illustration, the sensor for collecting user feedback 21 may comprise an electromyograph, a feedback thermometer, an electrodermograph, an electroencephalograph, a photoplethysmograph, an electrocardiogram, a pneumograph, a capnometer, a rheoencephalograph, hemoencephalogoraphy, a blood pressure monitor, a pulse rate monitor, a blood sugar level monitor, an Internet of Things (IoT) biometric sensor, or any of various combinations thereof.

The processor 12 is operatively coupled to the set of I/O interfaces 20 over a bus 14 that also couples additional system components, such as memory 16 (for example, random access memory (RAM) and storage system 18 (for example, read only memory (ROM), "flash" memory, and/or magnetic memory), to the processor 12. The processor 12 may execute the context determination software 13 and the machine learning algorithm 15 that performs one or more features or functions of the present invention. In some embodiments, one or more aspects of the context determination software 13 and/or the machine learning algorithm may be programmed into the integrated circuits of the processor 12, or loaded from memory 16, storage device 18, or network 24, or may be present in any of various combinations thereof.

Bus 14 may represent one or more of any of several types of bus structures, including a system bus, memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system of FIG. 5 may include a variety of computer system readable media. Such media may be any available media that is accessible by computer system, and it may include both volatile and non-volatile media, removable and non-removable media. System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (for example, a "hard drive"). Although not shown, a magnetic disk drive for reading from and writing to a removable, non-volatile magnetic disk (for example, a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system of FIG. 5 can communicate with one or more networks 24 such as a local area network (LAN), a general wide area network (WAN), and/or a public network (for example, the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method, comprising:
   receiving, by one or more processors, a user target cognitive state indicia identifying a target cognitive state of a user, and receiving a user cohort indicia identifying other persons having one or more common conditions or indicia in common with said user;

determining, by the one or more processors, a present user context, in response to said receiving a user target cognitive state indicia and the user cohort indicia;

performing a machine-learning procedure, by the one or more processors, to map the target cognitive state to a set of audio output characteristics based upon one or more parameters of the identified other persons from the received user cohort indicia and the present user context, said parameters comprising parameters obtained from an identified social media network associated with the user; and generating a context-sensitive soundscape with the set of audio output characteristics, based on the user target cognitive state indicia.

2. The computer-implemented method of claim 1 wherein the target cognitive state is selected from a group consisting of: relaxation, stimulation, falling asleep, and focusing on a task.

3. The computer-implemented method of claim 1 wherein the one or more common conditions of a user cohort indicia is selected from a group consisting of: demographic indicia, occupational indicia, medical or psychological indicia, cultural indicia, verbal language indicia, written language indicia, and medical history indicia.

4. The computer-implemented method of claim 1, wherein the set of audio output characteristics is selected from a group consisting of: music, environmental sounds, pink noise, white noise, another spectrally-shaped noise, ambient sounds of individuals engaging in an activity, and animal sounds.

5. The computer-implemented method of claim 1, wherein the performing of the machine-learning procedure is based on an assessment of user-related data.

6. The computer-implemented method of claim 1, further comprising collecting feedback and determining a level of effectiveness of the generated audio output characteristics for facilitating the target cognitive state, based on the collecting of the feedback.

7. The computer-implemented method of claim 1, further comprising using a multi-dimensional array configured for associating each of a respective plurality of cognitive states, including the target cognitive state, with at least one corresponding user cohort, at least one corresponding user medical or psychological condition, at least one corresponding user demographic, at least one corresponding task, or at least one context.

8. The computer-implemented method of claim 7, further comprising accessing the multi-dimensional array according to at least one learned useful value for an individual or a cohort.

9. The computer-implemented method of claim 1, wherein the set of audio output characteristics comprises a binaural beat comprising a first tone and a second tone, and the method further comprises feeding the first tone to a right-side element of a set of headphones, and feeding the second tone to a left-side element of the set of headphones, such that the first tone is fed to the right-side element for presentation to a right ear of the user, and the second tone is fed to the left-side element for presentation to a left ear of the user.

10. The computer-implemented method of claim 1, wherein the machine-learning procedure further comprises learning one or more SPLs; and modulating the one or more SPLs to enhance a noise masking.

11. The computer-implemented method of claim 1, wherein the machine-learning procedure further comprises modulating ambient noise.

12. A computer program product, the computer program product comprising a non-transitory computer-readable storage medium having a computer-readable program stored therein, wherein the computer-readable program, when executed on a computer including at least one processor, causes the at least one processor to:

receive a user target cognitive state indicia identifying a target cognitive state of a user, and receiving a user cohort indicia identifying other persons having one or more common conditions or indicia in common with said user;

determine a present user context, in response to said receiving a user target cognitive state indicia and the user cohort indicia in common with said user;

perform a machine-learning procedure, by the at least one processor, to map the target cognitive state to a set of audio output characteristics based upon one or more parameters of the identified other persons from the received user cohort indicia and the present user context, said parameters comprising parameters obtained from an identified social media network associated with the user; and generate a context-sensitive soundscape with the set of audio output characteristics, based on the user target cognitive state indicia.

13. The computer program product of claim 12 wherein the target cognitive state is selected from a group consisting of: relaxation, stimulation, falling asleep, and focusing on a task.

14. The computer program product of claim 12 wherein the one or more common conditions of a user cohort indicia that is selected from a group consisting of:

demographic indicia, occupational indicia, medical or psychological indicia, cultural indicia, verbal language indicia, written language indicia, and medical history indicia.

15. The computer program product of claim 12, wherein the set of audio output characteristics is selected from a group consisting of: music, environmental sounds, pink noise, white noise, another spectrally-shaped noise, ambient sounds of individuals engaging in an activity, and animal sounds.

16. The computer program product of claim 12, wherein the computer-readable program, when executed on the computer, causes the at least one processor to perform: the machine-learning procedure based on an assessment of user-related data.

17. The computer program product of claim 12, wherein the computer-readable program, when executed on the computer, causes the at least one processor to perform: collecting feedback and determining a level of effectiveness of the generated audio output characteristics for facilitating the target cognitive state, based on the collecting of the feedback.

18. The computer program product of claim 12, wherein the computer-readable program, when executed on the computer, causes the at least one processor to perform: using a multi-dimensional array configured for associating each of a respective plurality of cognitive states, including the target cognitive state, with at least one corresponding user cohort, at least one corresponding user medical or psychological condition, at least one corresponding user demographic, at least one corresponding task, or at least one context.

19. A system for generating a context-sensitive soundscape, the system comprising a computer including at least one processor and a memory coupled to the at least one processor, wherein the memory comprises instructions which, when executed by the at least one processor, cause the at least one processor to:
- receive a user target cognitive state indicia identifying a target cognitive state of a user, and receiving a user cohort indicia identifying other persons having one or more common conditions or indicia in common with said user;
- determine a present user context, in response to said receiving a user target cognitive state indicia and the user cohort indicia in common with said user;
- perform a machine-learning procedure, by the at least one processor, to map the target cognitive state to a set of audio output characteristics based upon one or more parameters of the identified other persons from the received user cohort indicia and the present user context, said parameters comprising parameters obtained from an identified social media network associated with the user; and
- generate a context-sensitive soundscape with the set of audio output characteristics, based on the user target cognitive state indicia.

20. The system of claim 19 wherein the target cognitive state is selected from a group consisting of: relaxation, stimulation, falling asleep, and focusing on a task.

* * * * *